(12) United States Patent
Chen et al.

(10) Patent No.: US 11,957,624 B2
(45) Date of Patent: Apr. 16, 2024

(54) ROLL-OFF FILM SYSTEM FOR GOGGLES

(71) Applicant: Xiamen Anbo Sports Goods Co., Ltd., Xiamen (CN)

(72) Inventors: Jalon Chen, Xiamen (CN); James Chen, Xiamen (CN); Xiaoqiang Shen, Xiamen (CN)

(73) Assignee: Xiamen Anbo Sports Goods Co., Ltd., Xiamen (CN)

( * ) Notice: Subject to any disclaimer, the term of this patent is extended or adjusted under 35 U.S.C. 154(b) by 92 days.

(21) Appl. No.: 17/944,969

(22) Filed: Sep. 14, 2022

(65) Prior Publication Data
US 2024/0082060 A1 Mar. 14, 2024

(51) Int. Cl.
*A61F 9/02* (2006.01)
*B08B 17/04* (2006.01)

(52) U.S. Cl.
CPC .............. *A61F 9/025* (2013.01); *B08B 17/04* (2013.01)

(58) Field of Classification Search
CPC .............. A61F 9/02; A61F 9/025; A61F 9/029
See application file for complete search history.

(56) References Cited

U.S. PATENT DOCUMENTS

| | | | |
|---|---|---|---|
| 9,839,558 B2 * | 12/2017 | Blanchard | A61F 9/025 |
| 10,342,704 B2 * | 7/2019 | Blanchard | A61F 9/028 |
| 10,357,400 B2 * | 7/2019 | Ginther | A61F 9/02 |
| 11,013,636 B2 * | 5/2021 | Sigismondo | A61F 9/022 |
| 11,337,859 B2 * | 5/2022 | Young | A61F 9/025 |
| 2013/0104299 A1 * | 5/2013 | Chen | A61F 9/029 2/431 |
| 2019/0142639 A1 * | 5/2019 | Durham | A61F 9/02 2/439 |
| 2021/0393440 A1 * | 12/2021 | Leatt | A61F 9/025 |
| 2022/0291529 A1 * | 9/2022 | Munn | G02C 13/006 |

* cited by examiner

*Primary Examiner* — F Griffin Hall
*Assistant Examiner* — Griffin Hall

(57) ABSTRACT

A roll-off film system for goggles includes a goggle and a roll off system. The roll off system includes a first cap, a second cap, a bridge, a first canister, a second canister and a fixation system. The first and the second caps are fixedly connected by the bridge, and the first and the second canisters are fixed on the goggle through the fixation system. Both ends of a bottom of the first cap are respectively provided with a fixation rib. Thus, the roll-off film and shaft are fixed on the first and second caps to obtain a set of accessories. After the roll-off film is used up, the old first and second caps with the roll-off film are directly removed, and a new set of accessories are mounted. Users replace the roll-off film simply and efficiently. The whole set of accessories are easily assembled and disassembled.

5 Claims, 9 Drawing Sheets

ROLL-OFF FILM SYSTEM FOR GOGGLES

TECHNICAL FIELD

The present disclosure relates to a roll-off film system, and more particularly to a roll-off film system for goggles.

BACKGROUND

The existing roll-off film system for goggles are complicated to assemble. The roll-off film needs to be assembled separately before being rolled onto two rotating shafts, then the roll-off films are assembled in canisters on both sides of the goggles, so the films are getting loose easily from the rotating shafts when assembled. The existing technology also has the following disadvantages.
  (1) After the roll-off film is used up, it is difficult to replace the film, which not only takes time and effort, but also the user needs to learn how to disassemble and assemble the film.
  (2) When the user replaces the roll-off film, if the whole system is replaced together, not only the cost is too high, but also it is difficult to disassemble.
  (3) Due to the difficult assembly process, it is prone to assemble wrongly, and shorten the lifetime of the roll-off film system, or damage roll-off film system to cause the roll-off film system complete failure.

SUMMARY

The objective of the present disclosure is to provide a roll-off film system to solve the disadvantages of the existing system proposed in the background art.

To achieve the above-mentioned objective, the present disclosure provides a roll-off film system for goggles, including:
  a goggle; and
  a roll off system;
  wherein the roll off system includes a first cap, a second cap, a bridge, a first canister, a second canister and a fixation system; the first cap and the second cap are fixedly connected by the bridge; and the first canister and the second canister are fixed on the goggle through the fixation system.

Both ends of a bottom of the first cap are respectively provided with a fixation rib; and ends of a bottom of the second cap are provided with a first receiving groove and a second receiving groove respectively; hooks are respectively disposed on bottoms of sides of the first cap and the second cap away from the bridge; and a second inner cap and a first inner cap are used to fix the film and shafts to the first cap and the second cap.

Sides of the first canister and the second canister away from the goggle are provided with a respective accommodating slot matching the corresponding hook, and the first canister and the second canister are provided with a respective guiding slot; and The fixation system comprises a cover plate, a locker, a connecting post, a fixation plate and a case, and the fixation plate is fixed on the goggle through the connecting post.

In an embodiment, the second canister is separably provided with a shaft; a straight slot is provided at a front end of the shaft; a front end of the second canister is movably mounted with a mechanism; and the front end of the shaft passes through the mechanism and extends to an inside thereof.

In an embodiment, a puller is movably connected to a right end of the mechanism.

In an embodiment, one end of the locker penetrates through the case to clamp with the connecting post, and the cover plate is configured to fix at a bottom of the case.

In an embodiment, both sides of the second inner cap and the first inner cap are fixedly connected with respective holding plates matching with the corresponding guiding slots.

Compared with the prior art, for roll-off film system for goggles, the first cap and the second cap are fixedly connected by the bridge, and the roll-off film and the shaft are fixed on the first and second caps to obtain a set of accessories. After the roll-off film is used up, the first and second caps with the roll-off film are removed, and a new set of accessories are mounted, and it can be used normally. Through the cooperation of various precision structures, users can replace the roll-off film more simply and efficiently. The whole set of accessories with the roll-off film can be easily assembled and disassembled. Even people who never uses the system can easily and efficiently replace it correctly. The roll-off film system can be prefabricated to satisfy quality standard without waste or damage.

In the Figures: 1, goggle; 2, roll off system; 3, first cap; 4, second cap; 5, bridge; 6, first canister; 7, second canister; 8, shaft; 9, mechanism; 10, puller; 11, hook; 12, first receiving groove; 13, second receiving groove; 14, fixation rib; 15, accommodating slot; 16, straight slot; 17, fixation system; 18, guiding slot; 19, cover plate; 20, locker; 21, connecting post; 22, fixation plate; 23, case; 24, holding plate; 25, first inner cap; 26, second inner cap.

DETAILED DESCRIPTION OF EMBODIMENTS

The technical solution in the present disclosure will be described clearly and completely below with reference to the accompanying drawings and embodiments. Obviously, the described embodiments are only some, but not all embodiments of the present disclosure. Based on the disclosed embodiments of the present disclosure, all other embodiments obtained by those skilled in the art without creative efforts shall fall within protection scope of the present disclosure.

Figure 1:
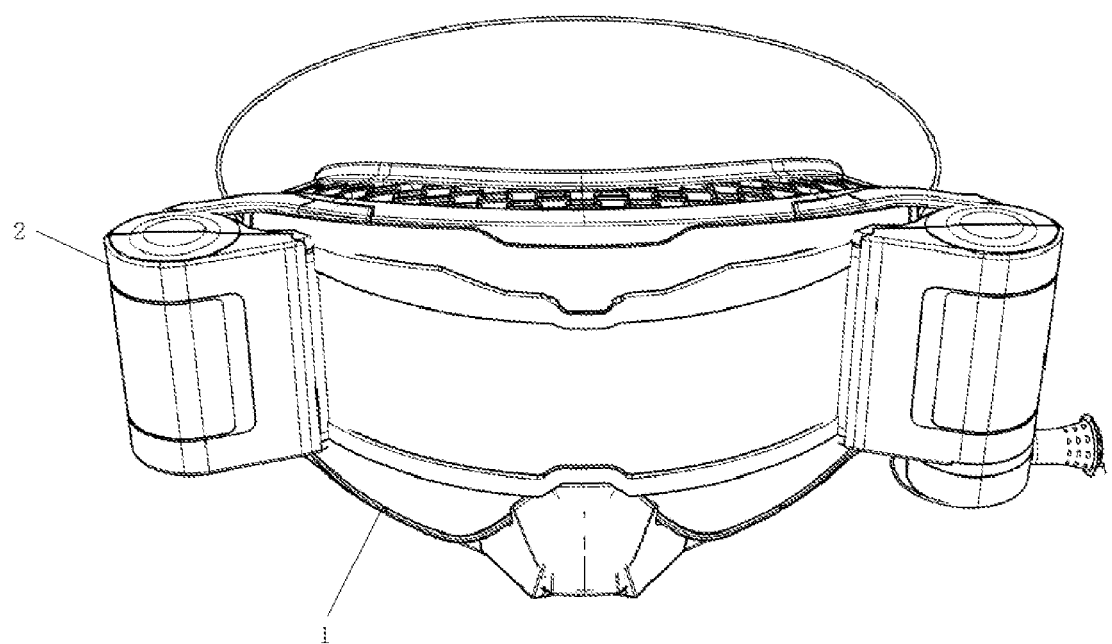
FIG. 1 is a front view of a roll-off film system for goggles according to one embodiment of the present disclosure.
Figure 2:
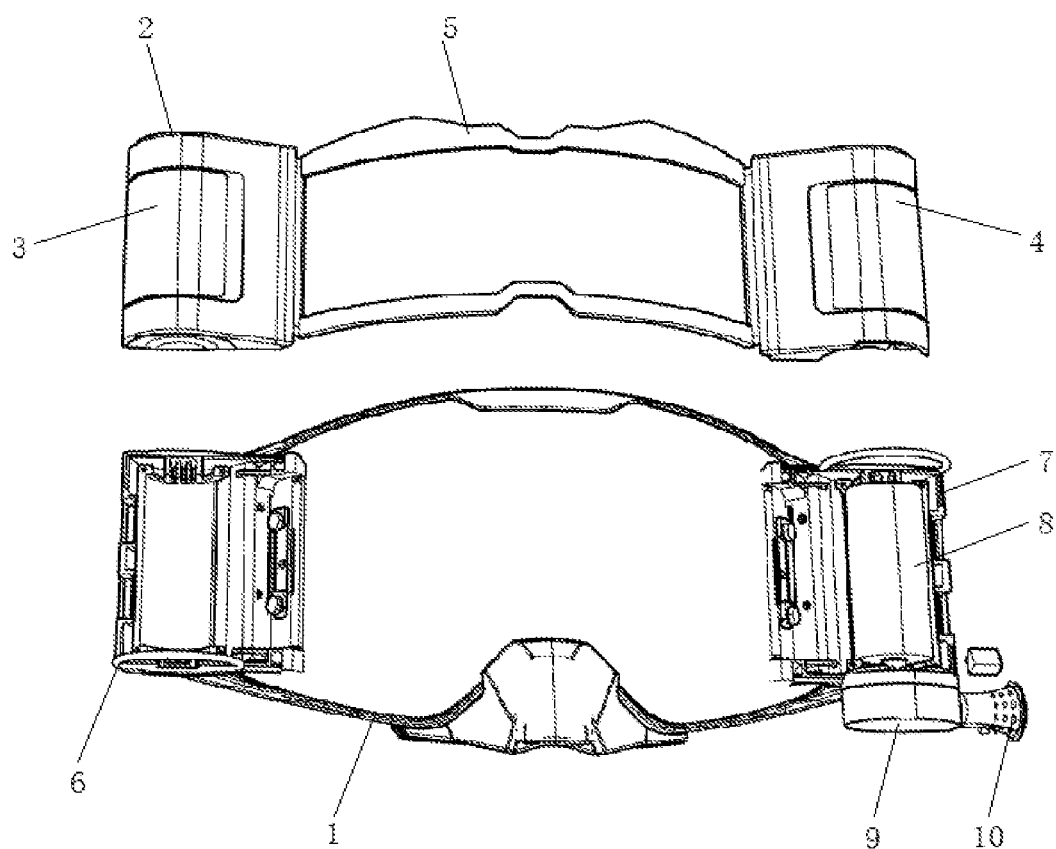
FIG. 2 is an exploded view of the roll-off film system for goggles according to one embodiment of the present disclosure.
Figure 3:
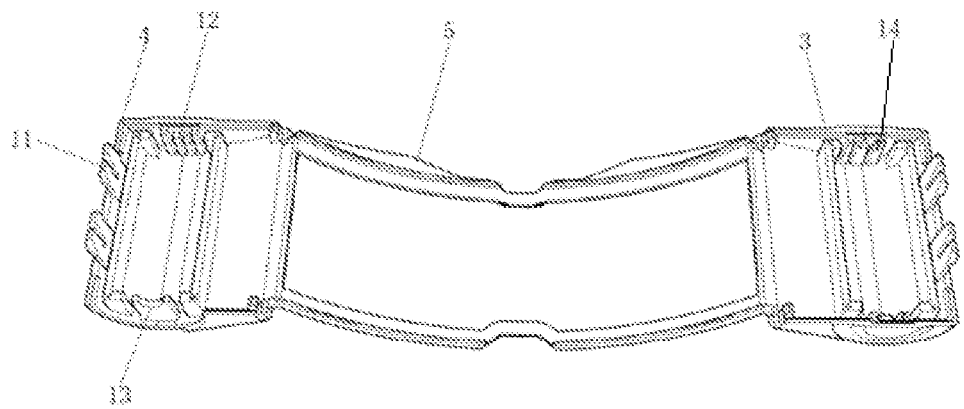
FIG. 3 is a bottom view of a first cap, a second cap and a bridge according to one embodiment of the present disclosure.
Figure 4:
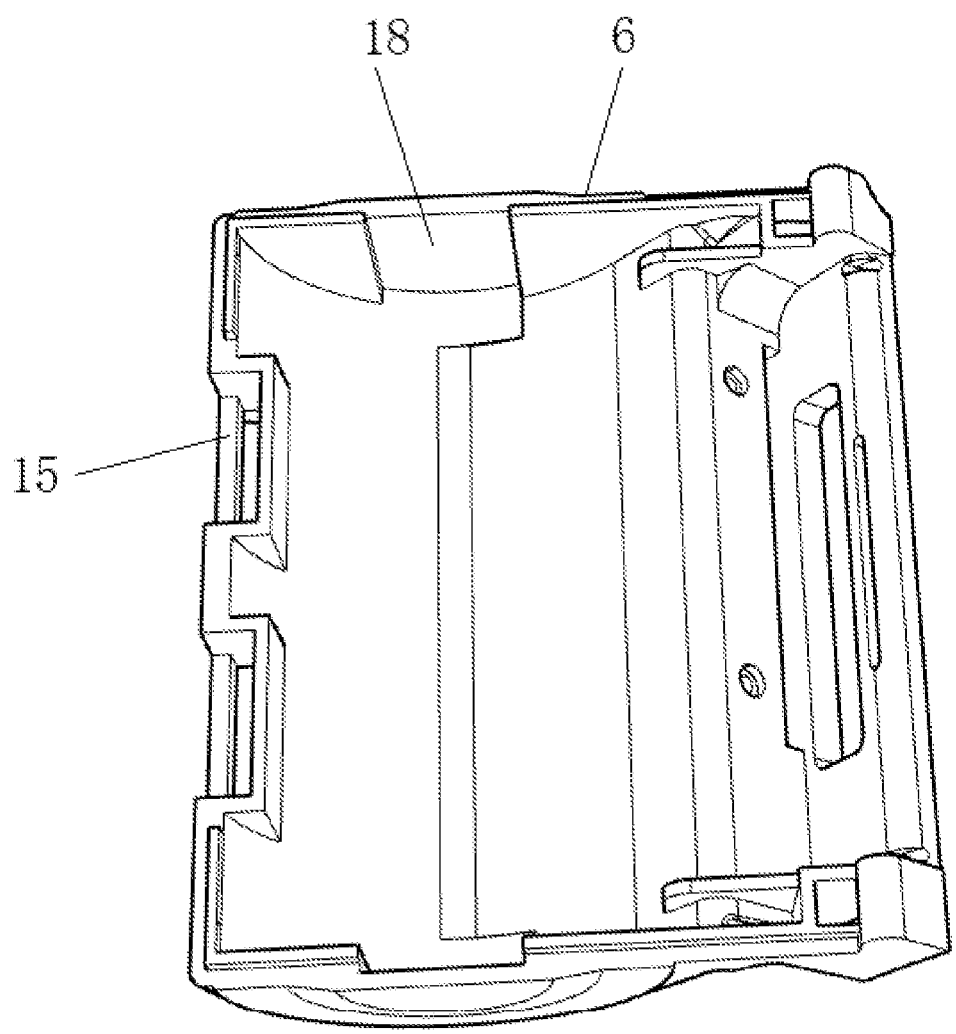
FIG. 4 is a structural diagram showing a first canister according to one embodiment of the present disclosure.
Figure 9:
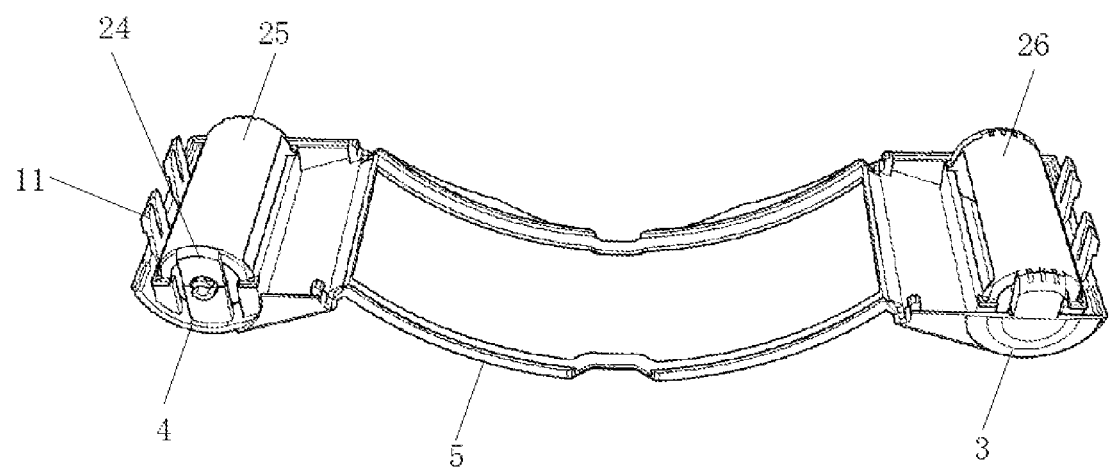
FIG. 9 is a structural diagram showing a back of the first cap and the second cap according to one embodiment of the present disclosure.

Referring to FIGS. 1-8, the present disclosure provides a roll-off film system for goggles which includes a goggle 1 and a roll off system 2. The roll off system 2 includes a first cap 3, a second cap 4, a bridge 5, a first canister 6, a second canister 7 and a fixation system 17. The first cap 3 and the second cap 4 are fixedly connected through the bridge 5, and the first canister 6 and the second canister 7 are respectively fixedly connected to the goggle 1 through the fixation system 17. Both ends of a bottom of the first cap 3 are respectively provided with the fixation ribs 14 which are used to prevent a roll-off film from getting loose. One end of a rotating shaft supporting the roll-off film is provided with holes matched with the fixation ribs 14. The fixation ribs 14 are matched with the holes to prevent the roll-off film from rotating in a reverse direction, and specifically, such a structure has a function similar to that of a ratchet and pawl mechanism. As shown in FIG. 3, ends of a bottom of the second cap 4 are respectively provided with a first receiving groove 12 and a second receiving groove 13. Hooks 11 are fixedly disposed on bottoms of sides of the first cap 3 and the second cap 4 away from the bridge 5. The sides of the first canister 6 and the second canister 7 away from the goggle 1 are provided with a respective accommodating slot 15. The accommodating slots 15 of the first canister 6 and the second canister 7 are matching with the corresponding hooks 11. The hooks 11 can be inserted into the corresponding accommodating slot 15 to realize connection between the first canister 6 and the first cap 3 and connection between the second canister 7 and the second cap 4. Front and rear sides of the first canister 6 and the second canister 7 are provided with a respective guiding slot 18. The guiding slots 18 are arranged for matching the holding plate 24 and the first receiving groove 12 for connection between the first canister 6 and the first cap 3 and connection between the second canister 7 and the second cap 4. The fixation system 17 includes a cover plate 19, a locker 20, a connecting post 21, a fixation plate 22 and a case 23. Specifically, the fixation plate 22 is fixedly connected to the goggle 1 through the connecting post 21. As shown in FIG. 9, a second inner cap 26 and a first inner cap 25 are respectively fixedly connected to bottoms of the first cap 3 and the second cap 4. Both sides of the second inner cap 26 and the first inner cap 25 are fixedly connected with holding plates 24 matching with the guiding slots 18.

In FIG. 2, the first cap 3, the second cap 4 and the bridge 5 are arranged for mounting the roll-off film. When the goggle needs to be replaced with the roll-off film, the first and second caps with the roll-off film will be completely replaced. The systems on both sides of the goggle are connected by a bridge or in other means to ensure modularity and stability as well as simplicity in the process of replacing the roll-off film.

Figure 5:
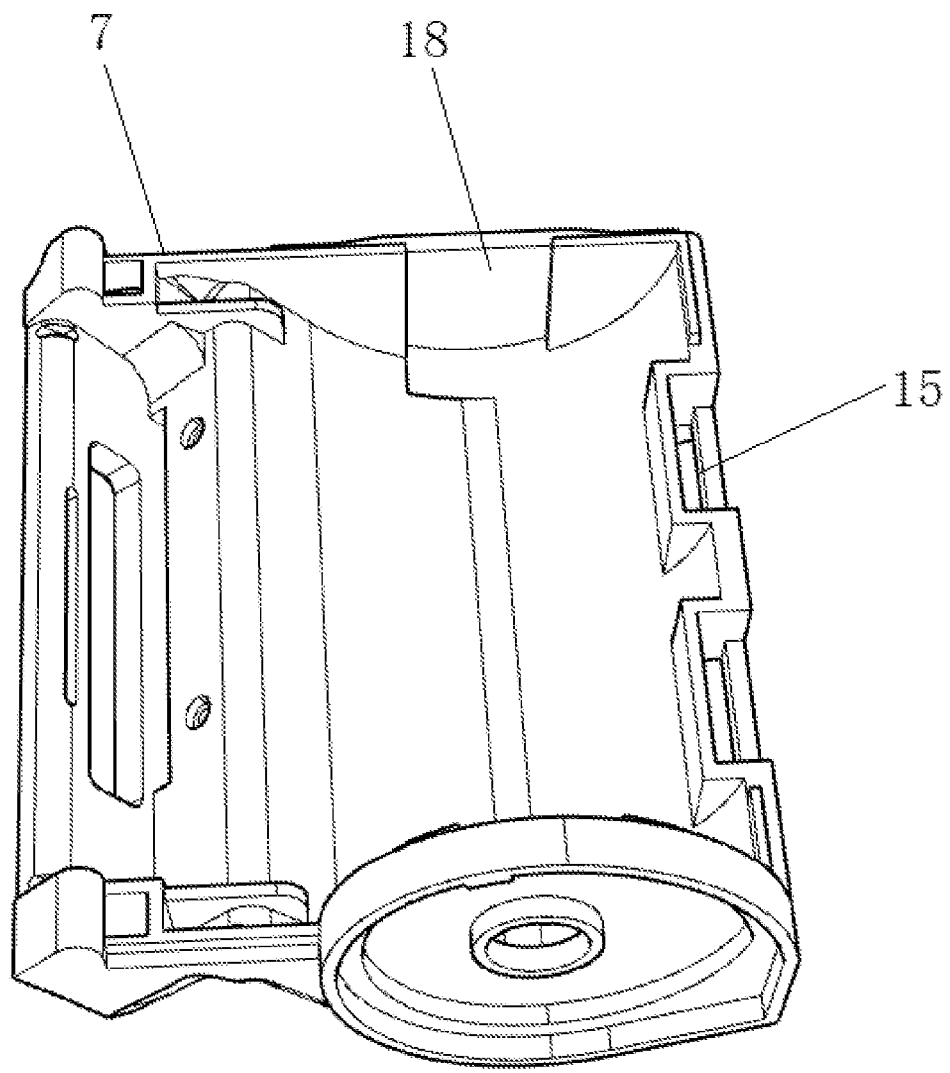
FIG. 5 is a structural diagram showing a second canister according to one embodiment of the present disclosure.
Figure 6:
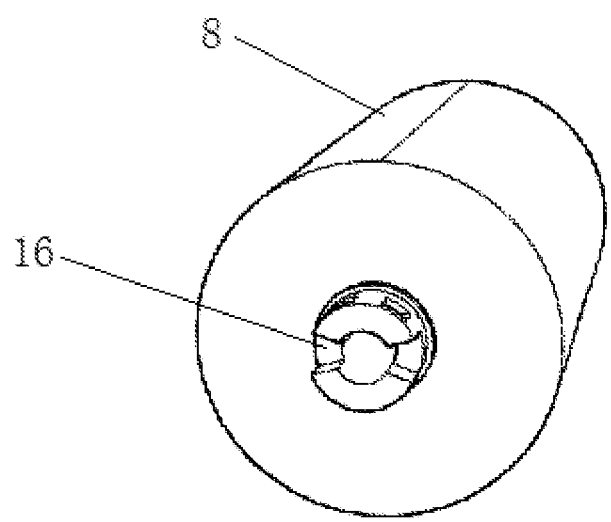
FIG. 6 is a structural diagram showing a shaft according to one embodiment of the present disclosure.
Figure 7:
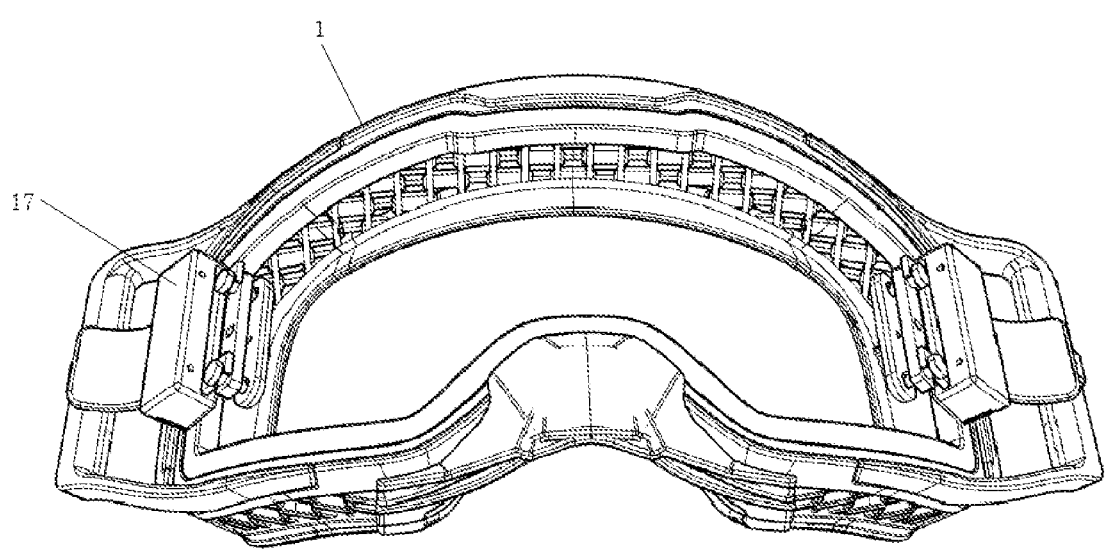
FIG. 7 is a structural diagram showing a fixation system on a goggle according to one embodiment of the present disclosure.
Figure 8:
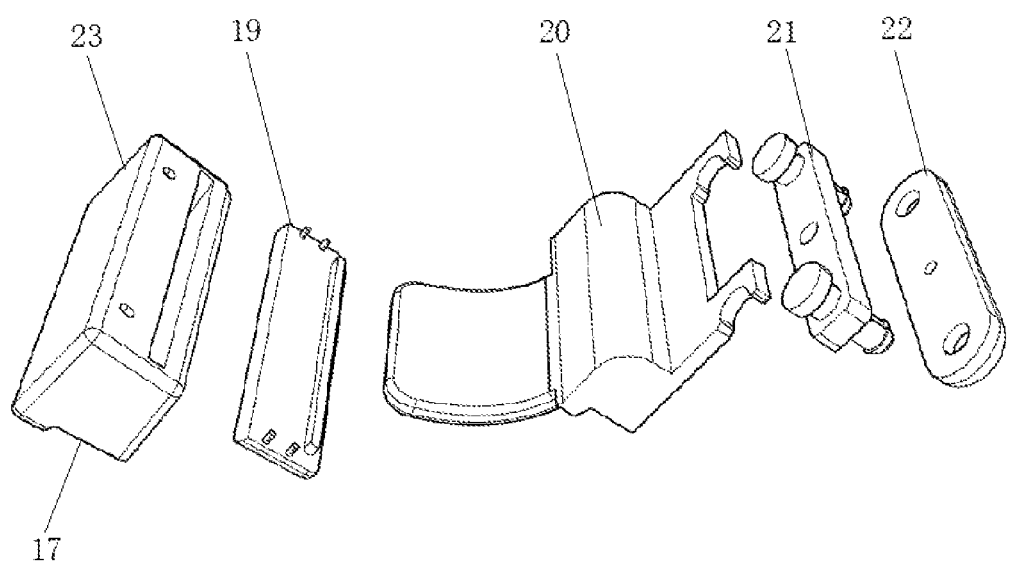
FIG. 8 is an exploded view of the fixation system according to one embodiment of the present disclosure.

In FIG. 5, the first cap 3 and the second cap 4 are fixed by screws, but not limited to it. A roll-off film is provided on the shaft 8.

Referring to FIGS. 2 and 6 again, the second canister 7 is separably provided with a shaft 8. A straight slot 16 is opened at a front end of the shaft 8. The front end of the shaft 8 penetrates a mechanism 9 and extends to the inside thereof. A front end of the second canister 7 is movably mounted with a mechanism 9, and the straight slot 16 is used to cooperate with an output end of the mechanism 9 to replace the roll-off film.

A puller 10 is movably connected to a right end of the mechanism 9. By pulling the puller 10, the shaft 8 is rotated to replace the roll-off film. After the puller 10 is released, the puller 10 will be automatically reset under the action of an elastic member inside the mechanism 9. The collecting film method is the prior art, so it will not be repeated here.

One end of the locker 20 penetrates through the case 23 and is clamped with the connecting post 21, and the cover plate 19 is movably connected to the bottom of the case 23.

Thus, for the roll-off film system for goggles, the first cap and the second cap are fixedly connected by the bridge, the roll-off film and the shaft are fixed on the first and second caps to obtain a set of accessories. After the roll-off film is used up, the first and second caps with the roll-off film are directly removed, and a new set of accessories are mounted, and it can be used normally. Through the cooperation of various precision structures, users can replace the roll-off film more simply and efficiently. The whole set of accessories having the roll-off film can be easily assembled and disassembled. Even people who never uses the system can easily and efficiently replace it correctly. The roll-off film system can be prefabricated to satisfy quality standard without waste or damage.

While the present disclosure has been described in detail with reference to the embodiments, it should be understood that it is still possible to modify the technical solutions in the foregoing embodiments, or perform replacements to some of the technical features. Understandably, any modifications and replacements made by those skilled in the art without departing from the spirit of the disclosure should fall within the scope of the disclosure defined by the present claims.

What is claimed is:

1. A roll-off film system for goggles, comprising:
a goggle (1); and
a roll off system (2);
wherein the roll off system (2) comprises a first cap (3), a second cap (4), a bridge (5), a first canister (6), a second canister (7) and a fixation system (17), the first cap (3) and the second cap (4) are fixedly connected by the bridge (5), and the first canister (6) and the second canister (7) are fixed on the goggle (1) through the fixation system (17);
both ends of a bottom of the first cap (3) are respectively provided with a fixation rib (14), ends of a bottom of the second cap (4) are respectively provided with a first receiving groove (12) and a second receiving groove (13), a hook (11) is respectively disposed on bottoms of sides of the first cap (3) and the second cap (4) away from the bridge (5), and a second inner cap (26) and a first inner cap (25) are respectively fixedly connected to bottoms of the first cap (3) and the second cap (4);
sides of the first canister (6) and the second canister (7) away from the goggle (1) are provided with a respective accommodating slot (15) matching the corresponding hook (11), and the first canister (6) and the second canister (7) are provided with a respective guiding slot (18); and
the fixation system (17) comprises a cover plate (19), a locker (20), a connecting post (21), a fixation plate (22) and a case (23), and the fixation plate (22) is fixed on the goggle (1) through the connecting post (21).

2. The roll-off film system for goggles according to claim 1, wherein the second canister (7) is separably provided with a shaft (8), a straight slot (16) is provided at a front end of the shaft (8), a front end of the second canister (7) is movably mounted with a mechanism (9), and the front end of the shaft (8) passes through the mechanism (9) and extends to an inside thereof.

3. The roll-off film system for goggles according to claim 2, wherein a puller (10) is movably connected to a right end of the mechanism (9).

4. The roll-off film system for goggles according to claim 1, wherein one end of the locker (20) penetrates through the case (23) to clamp with the connecting post (21), and the cover plate (19) is configured to fix at a bottom of the case (23).

5. The roll-off film system for goggles according to claim 1, wherein both sides of the second inner cap (26) and the first inner cap (25) are fixedly connected with respective holding plates (24) matching with the corresponding guiding slots (18).

\* \* \* \* \*